(12) United States Patent
Mikhail et al.

(10) Patent No.: US 9,782,259 B2
(45) Date of Patent: Oct. 10, 2017

(54) GRAFT COLLECTION AND CONTAINMENT SYSTEM FOR BONE DEFECTS

(71) Applicant: DePuy Synthes Products, LLC, Raynham, MA (US)

(72) Inventors: George Mikhail, West Chester, PA (US); Ross Hamel, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 508 days.

(21) Appl. No.: 14/463,404

(22) Filed: Aug. 19, 2014

(65) Prior Publication Data

US 2014/0364961 A1 Dec. 11, 2014

Related U.S. Application Data

(63) Continuation of application No. 13/296,471, filed on Nov. 15, 2011, now Pat. No. 8,840,614.

(Continued)

(51) Int. Cl.
*A61B 10/02* (2006.01)
*A61F 2/28* (2006.01)
(Continued)

(52) U.S. Cl.
CPC ............ *A61F 2/2846* (2013.01); *A61B 10/02* (2013.01); *A61F 2/2803* (2013.01); *A61F 2/4644* (2013.01); *A61B 2010/0258* (2013.01); *A61F 2002/2825* (2013.01); *A61F 2002/2835* (2013.01); *A61F 2002/3024* (2013.01); *A61F 2002/30062* (2013.01); *A61F 2002/30462* (2013.01); *A61F 2002/30471* (2013.01); *A61F 2002/30578* (2013.01); *A61F 2002/30599* (2013.01); *A61F 2002/30909* (2013.01); *A61F 2002/30948* (2013.01); *A61F 2002/30975* (2013.01); *A61F 2002/4685* (2013.01); *A61F 2310/00041* (2013.01); *A61F 2310/00179* (2013.01); *A61F 2310/00359* (2013.01); *A61F 2310/00365* (2013.01)

(58) Field of Classification Search
CPC .................. A61B 10/02; A61B 2010/0258
See application file for complete search history.

(56) References Cited

U.S. PATENT DOCUMENTS 4,553,553 A * 11/1985 Homann ................ C12M 23/10
600/562
4,834,703 A * 5/1989 Dubrul ................... A61B 10/02
604/48

(Continued)

FOREIGN PATENT DOCUMENTS

CN 1046278 10/1990
CN 101103942 1/2008
(Continued)

*Primary Examiner* — Nicholas Woodall
(74) *Attorney, Agent, or Firm* — Fay Kaplun & Marcin, LLP

(57) ABSTRACT

A device for containing bone graft material comprises a body including an inner sleeve extending longitudinally from a proximal end to a distal end and an outer sleeve surrounding the inner sleeve and extending longitudinally from a proximal end to a distal end such that a bone graft collecting space is formed therebetween.

12 Claims, 18 Drawing Sheets

Related U.S. Application Data

(60) Provisional application No. 61/413,590, filed on Nov. 15, 2010.

(51) Int. Cl.
*A61F 2/46* (2006.01)
*A61F 2/30* (2006.01)

(56) References Cited

U.S. PATENT DOCUMENTS

| | | | |
|---|---|---|---|
| 5,211,664 | A | 5/1993 | Tepic et al. |
| 6,022,354 | A | 2/2000 | Mercuri et al. |
| 6,299,763 | B1 | 10/2001 | Ashman |
| 6,387,057 | B1 | 5/2002 | Heske |
| 6,387,070 | B1 | 5/2002 | Marino et al. |
| 6,406,454 | B1 | 6/2002 | Hajianpour |
| 6,468,225 | B1 | 10/2002 | Lundgren |
| 6,767,354 | B2 | 7/2004 | Johanson et al. |
| 7,204,810 | B2 | 4/2007 | Hynes et al. |
| 7,556,622 | B2 | 7/2009 | Mark et al. |
| 7,621,917 | B2 | 11/2009 | Geneve et al. |
| 2002/0123750 | A1 | 9/2002 | Eisermann et al. |
| 2005/0273165 | A1 | 12/2005 | Griffiths et al. |
| 2006/0052760 | A1* | 3/2006 | Batzdorf ............ A61F 2/4644 604/319 |
| 2006/0056270 | A1* | 3/2006 | Lee ................. A61B 10/025 366/139 |
| 2006/0213374 | A1 | 9/2006 | Shippert |
| 2007/0185585 | A1 | 8/2007 | Bracy et al. |
| 2007/0225665 | A1 | 9/2007 | Perez-Cruet et al. |
| 2007/0225686 | A1* | 9/2007 | Shippert ............ A61M 1/0001 604/542 |
| 2008/0071192 | A1 | 3/2008 | Hynes et al. |
| 2008/0172095 | A1 | 7/2008 | Salerni et al. |

FOREIGN PATENT DOCUMENTS

| | | |
|---|---|---|
| DE | 4106881 | 8/1992 |
| DE | 19633865 | 2/1998 |
| EP | 0417330 | 3/1991 |
| EP | 0493698 | 7/1992 |
| EP | 0551611 | 7/1993 |
| EP | 0553517 | 8/1993 |
| EP | 0605799 | 7/1994 |
| EP | 0711535 | 5/1996 |
| EP | 0758551 | 2/1997 |
| EP | 0955022 | 11/1999 |
| EP | 0968692 | 1/2000 |
| EP | 1216666 | 6/2002 |
| EP | 1321115 | 6/2003 |
| EP | 1523963 | 4/2005 |
| EP | 1574174 | 9/2005 |
| EP | 1623727 | 2/2006 |
| EP | 1867292 | 12/2007 |
| EP | 2110087 | 10/2009 |
| FR | 2801783 | 6/2001 |
| FR | 2815845 | 5/2002 |
| FR | 2848414 | 6/2004 |
| GB | 2387117 | 10/2003 |
| JP | S6485645 | 3/1989 |
| JP | H05184594 | 7/1993 |
| JP | 2523686 | 8/1996 |
| JP | 2539725 | 10/1996 |
| JP | H1147170 | 2/1999 |
| JP | 3692216 | 9/2005 |
| JP | 4024307 | 12/2007 |
| JP | 2009506845 | 2/2009 |
| WO | 88/01517 | 3/1988 |
| WO | 96/09079 | 3/1996 |
| WO | 97/23174 | 7/1997 |
| WO | 97/39685 | 10/1997 |
| WO | 97/42912 | 11/1997 |
| WO | 98/38948 | 9/1998 |
| WO | 98/38949 | 9/1998 |
| WO | 99/13805 | 3/1999 |
| WO | 01/28460 | 4/2001 |
| WO | 02/34168 | 5/2002 |
| WO | 02/34170 | 5/2002 |
| WO | 02/39946 | 5/2002 |
| WO | 02/058529 | 8/2002 |
| WO | 03/057046 | 7/2003 |
| WO | 2004/030548 | 4/2004 |
| WO | 2004/064691 | 8/2004 |
| WO | 2005/069924 | 8/2005 |
| WO | 2005/070347 | 8/2005 |
| WO | 2005/086849 | 9/2005 |
| WO | 2006/023156 | 3/2006 |
| WO | WO2007028140 | 3/2007 |

* cited by examiner

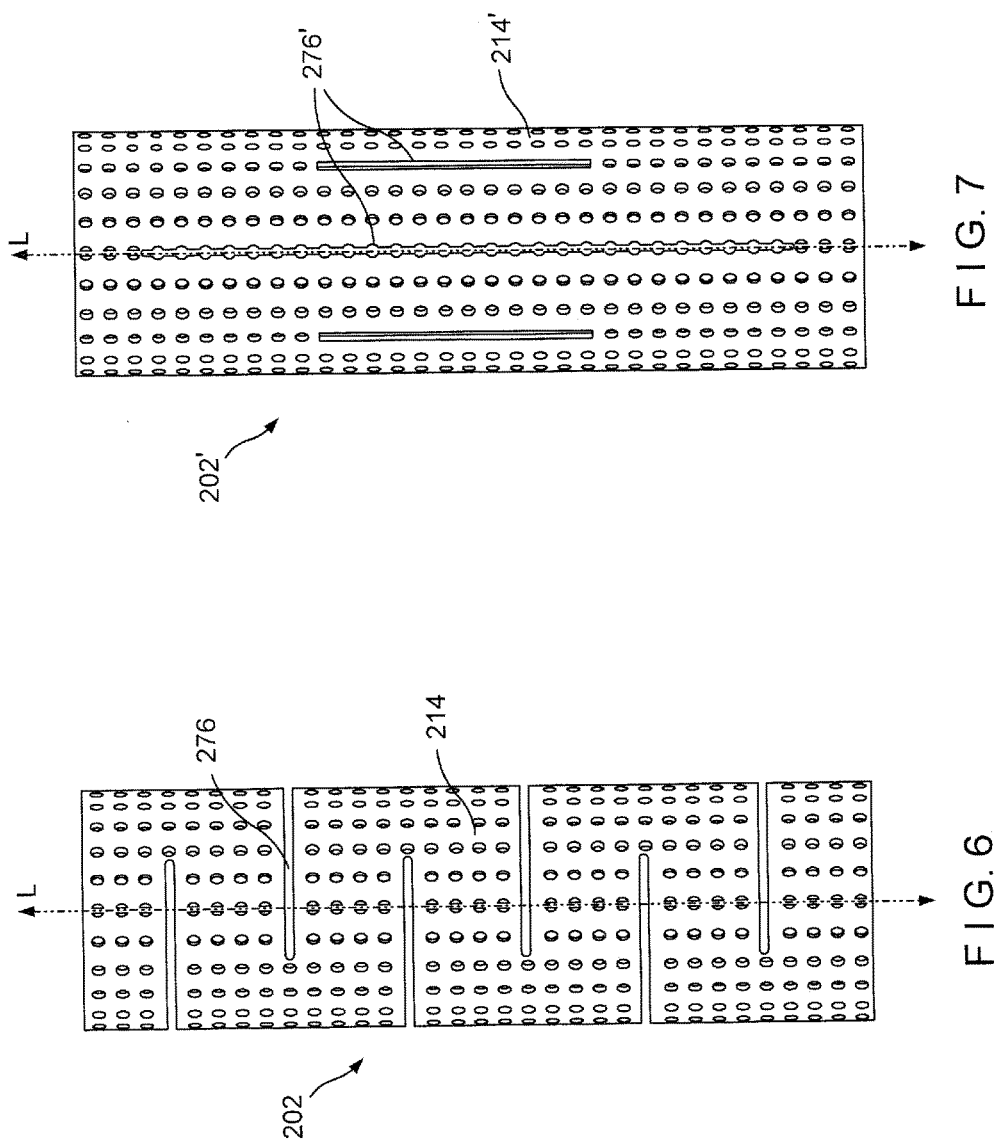

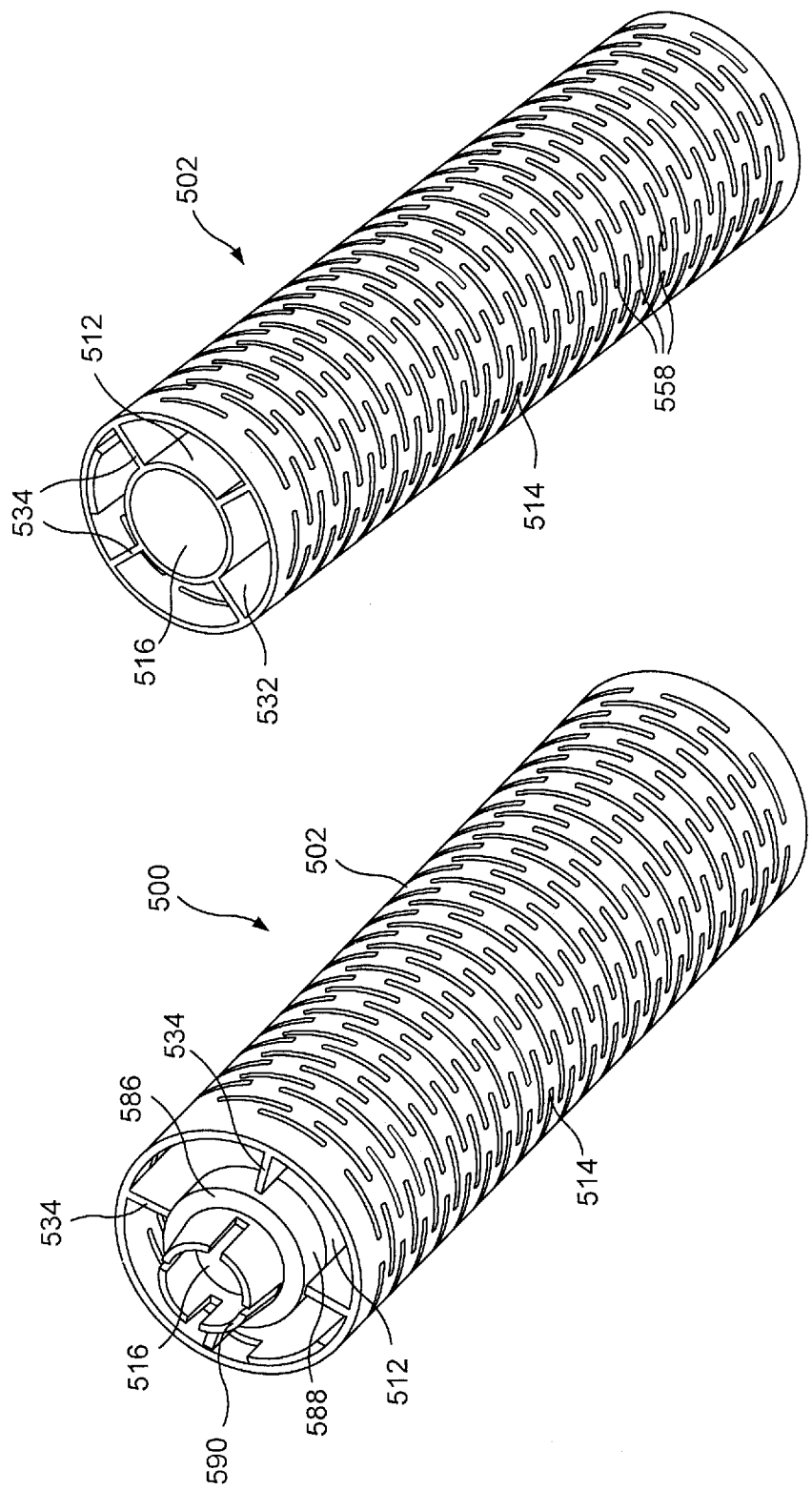

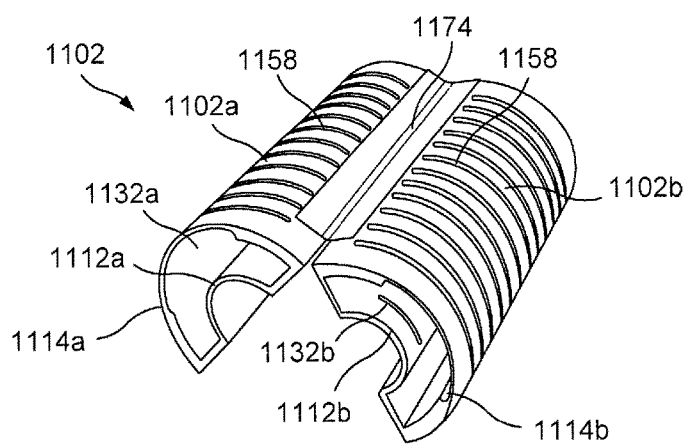
F I G. 24
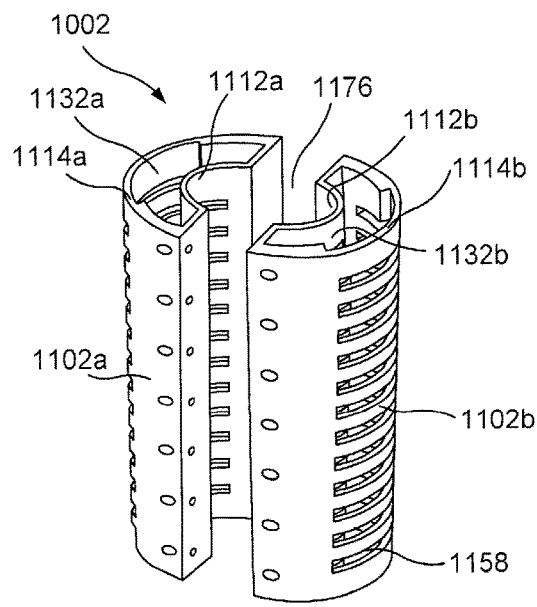
F I G. 25
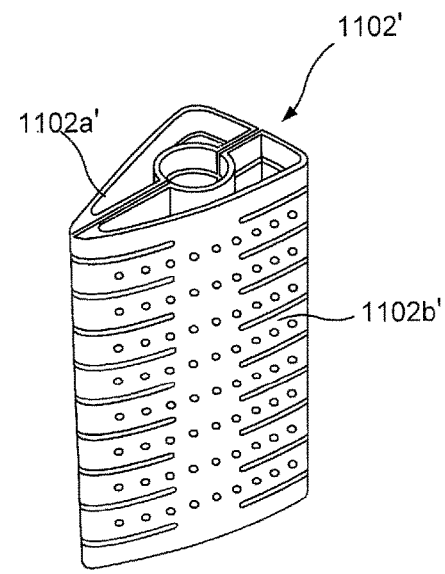
F I G. 26

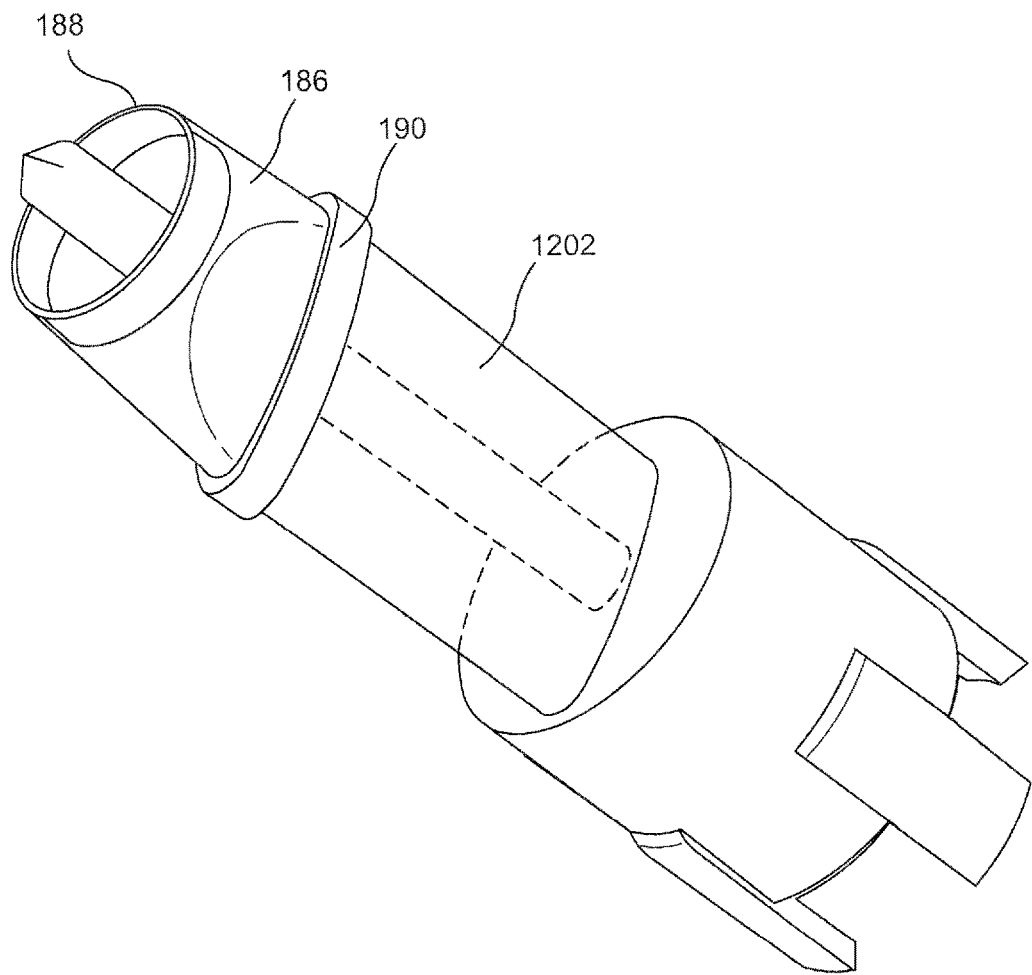
F I G. 29

GRAFT COLLECTION AND CONTAINMENT SYSTEM FOR BONE DEFECTS

The present application is a Continuation Application of U.S. patent application Ser. No. 13/296,471 filed on Nov. 15, 2011, now U.S. Pat. No. 8,840,614; which claims priority to U.S. Provisional Application Serial No. 61/413,590 filed on Nov. 15, 2010. The disclosures of the above patent(s)/applications are incorporated herein by reference.

BACKGROUND

Field of the Invention

The present invention relates to the treatment of bone defects and, in particular, relates to treatments using bone grafts.

Background

Large bone defects are often treated with metal implants and/or bone grafts to assist with healing of the bone. The bone grafts may be placed in the target area using any of a variety of methods. For example, a graft may simply be placed between two separated ends of an injured or otherwise damaged bone. However, without a container for the bone graft, the graft may fall away before it can be utilized by the body. According to another method, PMMA spacers may be placed in the target area so that the body may form its own fibrous tissue within the spacers. Subsequently, the PMMA spacers are removed and bone graft material is packed into the capsule formed by the body. Alternatively, some methods have included a mesh placed into the target area to contain the bone graft material at that location. These mesh containers generally include an outer wall with a diameter selected to match an outer surface of the bone to prevent the graft material from falling out of the bone.

SUMMARY OF THE INVENTION

The present invention is directed to a device for containing bone graft material comprising a body including an inner sleeve extending longitudinally from a proximal end to a distal end and an outer sleeve surrounding the inner sleeve and extending longitudinally from a proximal end to a distal end such that a bone graft collecting space is formed therebetween.

BRIEF DESCRIPTION OF THE DRAWINGS

FIG. 6 shows a side view of a graft container according to a second exemplary embodiment of the present invention;

FIG. 7 shows a side view of the graft container of FIG. 6 according to a third exemplary embodiment of the present invention;

FIG. 13 shows a perspective view of an assembled graft container and tip according to a ninth exemplary embodiment of the present invention;

FIG. 14 shows a perspective view of the graft container of FIG. 13;

FIG. 24 shows a perspective view of a graft container according to a fifteenth exemplary embodiment of the present invention;

FIG. 25 shows a perspective view of the graft container of FIG. 24, a first and second clam-shell portion thereof separated from one another;

FIG. 26 shows a perspective view of a graft container according to a sixteenth exemplary embodiment of the present invention;

FIG. 29 shows a perspective view of an adaptor for the system of FIG. 1, according to a further embodiment of the present invention.

DETAILED DESCRIPTION

Figure 1:
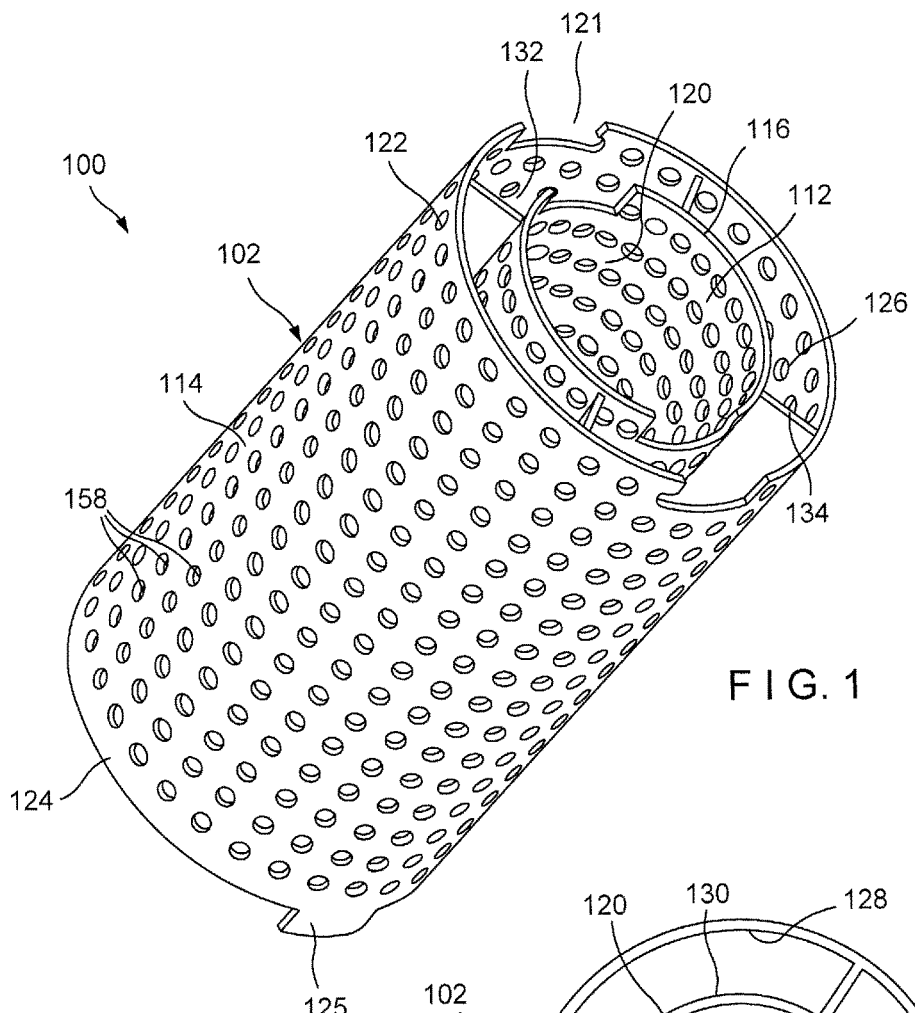
FIG. 1 shows a perspective view of a graft container according to a first exemplary embodiment of the present invention.

The present invention may be further understood with reference to the following description and the appended drawings, wherein like elements are referred to with the same reference numerals. The present invention relates to the treatment of bone defects and, in particular, relates to treatments using bone grafts. Exemplary embodiments of the present invention describe a bone graft collection and containment system comprising a double-walled graft container for receiving and holding graft material between an inner and outer wall thereof to prevent excess graft material from being lost in a medullary canal of the target bone and to facilitate the flow of nutrients to the graft.

Figure 2:
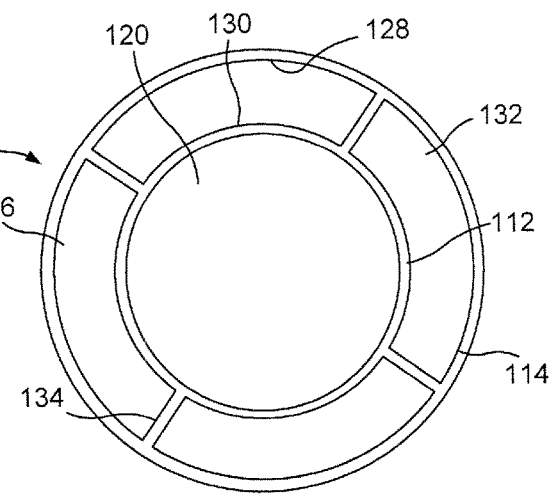
FIG. 2 shows a top view of the graft container of FIG. 1.

As shown in FIGS. 1-2, a graft system 100 comprises a graft container 102 configured to be positioned between separated longitudinal portions of a hone at a target spot at which a graft is to be made to join the separated portion of the target bone. For example, the container 102 may be formed as a double-walled vessel sized and shaped to match the contours of the target bone. Specifically, an outer sleeve 114 of the container 102 is preferably shaped to substantially match a profile of outer surfaces of the target portions of bone adjacent to the site of the graft. For a long tubular bone, the outer sleeve 114 will be substantially cylindrical with an outer diameter substantially matching that of the adjacent portions of bone. The container 102 further includes an inner sleeve 112 separated from the outer sleeve 114 by an annular space 132 within which bone graft material is to be held. The inner sleeve 112 is substantially tubular with a diameter selected to substantially match an inner diameter of a medullary canal of the bone to prevent bone graft material from being lost from the graft into the medullary canal enhancing the incorporation of the graft material into the bone.

The inner sleeve 112 of the container 102 extends longitudinally from a proximal end 116 to a distal end 118 and defines a central lumen 120 radially therewithin. In a preferred embodiment, the container 102 may be sized and shaped for treating a femur. For example, the inner and outer sleeves 114, 112 may be substantially tubular and substantially equal to one another in length such that proximal ends 116, 122 correspond to one another in position longitudinally and distal ends 118, 124 also correspond to one another in position longitudinally. The inner and outer sleeves 112, 114 are connected to one another via one or more ribs 134 extending between the inner and outer sleeves 112, 114 along at least a portion of the length thereof. In a preferred embodiment, the container 102 includes four ribs 134 connecting the inner and outer sleeves 112, 114, which are equally spaced relative to one another about a circumference of the container 102. A diameter of an inner surface 128 of the lumen 126 of the outer sleeve 114 is larger than a diameter of an outer surface 130 of the inner sleeve 112 by an amount selected to form an annular space 132 therebetween for collecting the bone graft material.

The container 102 may further include a notch 121 extending through at least one of the proximal ends 116, 122 of the inner and outer sleeves 112, 114, respectively, and a tab 125 extending distally from at least one of the distal ends 118, 124 the inner and outer sleeves 112, 114, respectively. The notch 121 and the tab 125 may correspond in size and shape such that, if desired, one ore more containers 102 may be stacked longitudinally to increase a bone graft length. The notch 121 of a first container 102 interfaces with the tab 125 of a second container 102. In a preferred embodiment, the container 102 includes two notches 121 diametrically opposed to one another and two tabs 125 similarly diametrically opposed to one another.

The inner and outer sleeves 112, 114 preferably include holes 158 extending therethrough to permit evacuation of blood and irrigation fluids during graft material collection, while also permitting nutrients to flow into the bone graft material collected in the space 132 from radially outside and inside the container 102. It will be understood by those of skill in the art that the hoes 158 are sized to permit the flow of nutrients therethrough while preventing the bone graft material from passing therethrough. For example, the diameter of the holes may be in the range of 0.5 to 2.0 mm and spaced apart from one another in a range of between 4.0 mm to 8.0 mm. As would be understood by those skilled in the art, the container 102 may be formed of any suitably strong bio-compatible material such as a polymer or a metal and may also be bioresorbable. In another embodiment, the inner and outer sleeves 112, 114 may be formed of a porous material or mesh material so that holes 158 are not necessary. In yet another embodiment, the container 102 may be formed of a flexible material. In one exemplary embodiment, the outer sleeve 114 may be formed of a substantially rigid material while the inner sleeve 112 is formed of a flexible material such that the inner sleeve 112 may adapt to a size and shape of for example, an intramedullary rod inserted through a medullary canal of a bone. The container 102 may be formed of polymer materials such as, for example, Polyglycolic Acid (PGA), Poly Lactic Acid (PLA), Polycaprolactone (PCL) or any similarly acting polymers or copolymers. The container 102 may also be formed of collagen or polyurethane. The container 102 may also be formed of a metal such as, for example, a bioresorbable magnesium or non-resorbable metals such as an implantable titanium or stainless steel. In yet another embodiment, the container 102 may be fabricated from donor bone, e.g., specifically fabricated allograft or xenograft materials. In another embodiment, the container 102 may be formed of materials such as ceramic or polyetherertherketone (PEEK).

Figure 3:
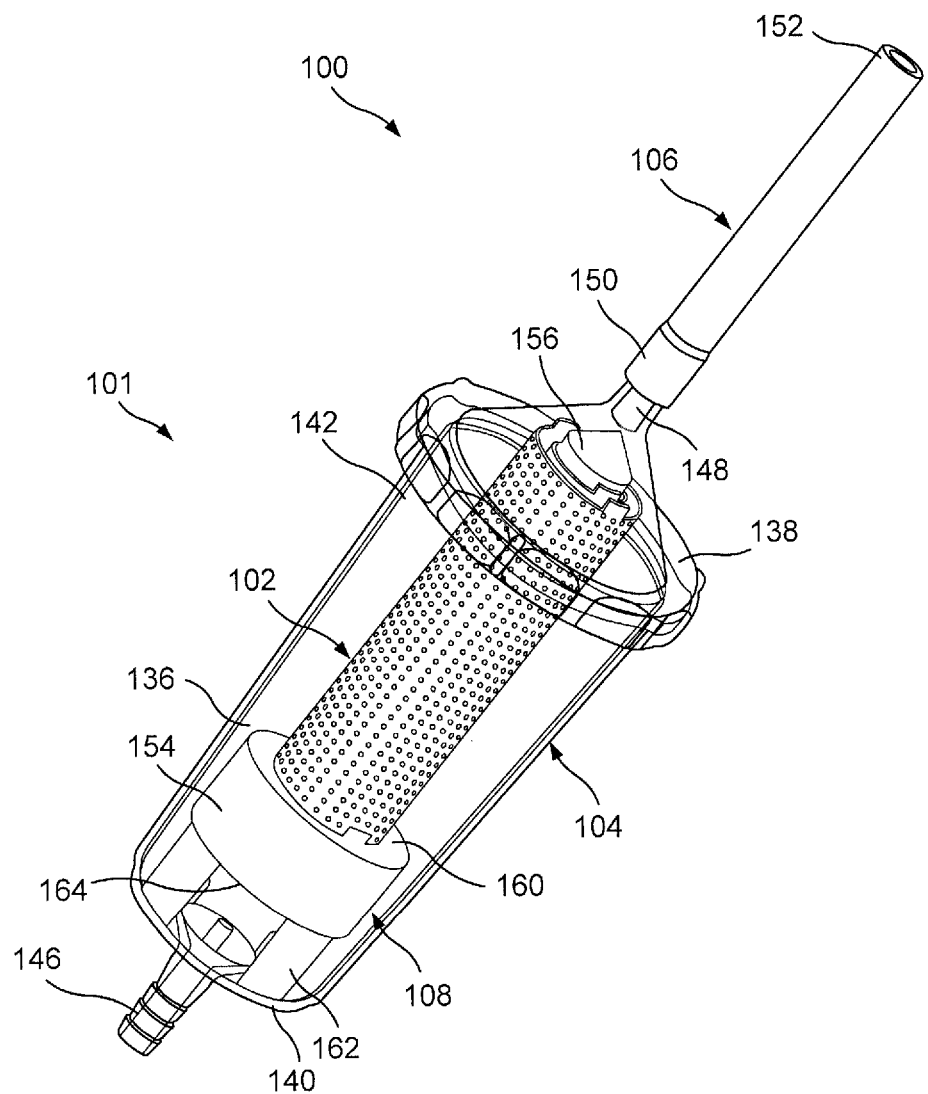
FIG. 3 shows a perspective view of the graft container of FIG. 1 with a graft collection system according to the present embodiment.
Figure 4:
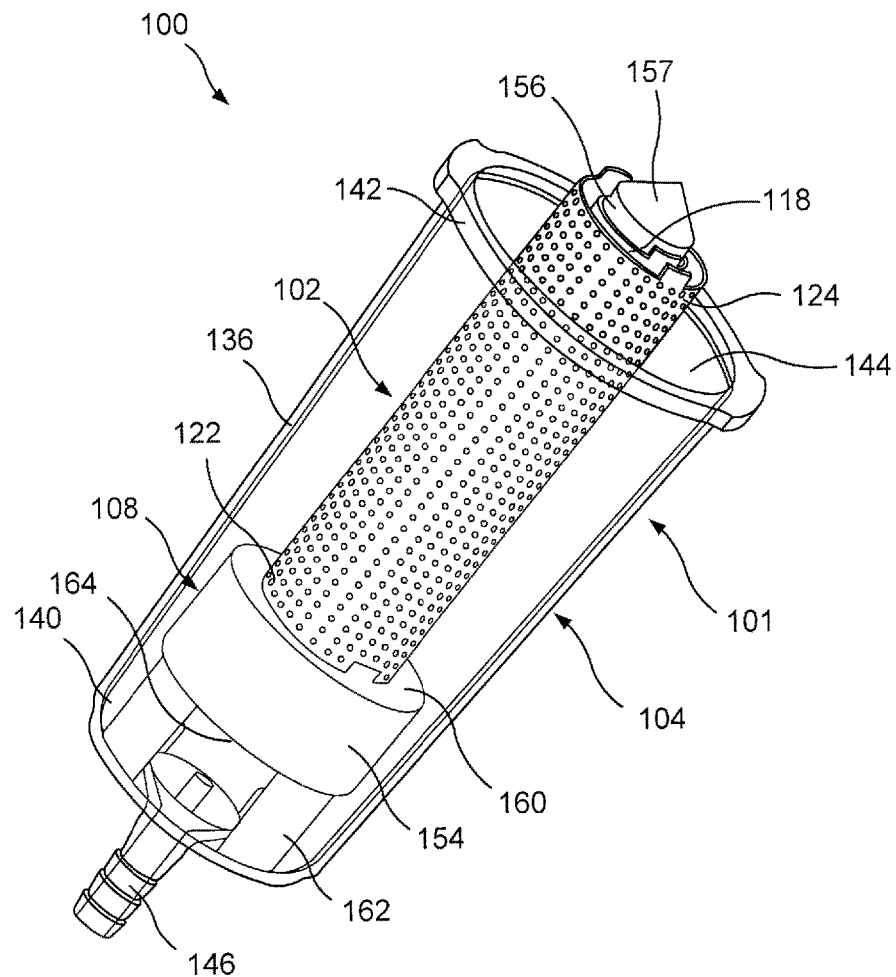
FIG. 4 shows a perspective view of the graft container and collection system of FIG. 3, with a cover removed.
Figure 5:
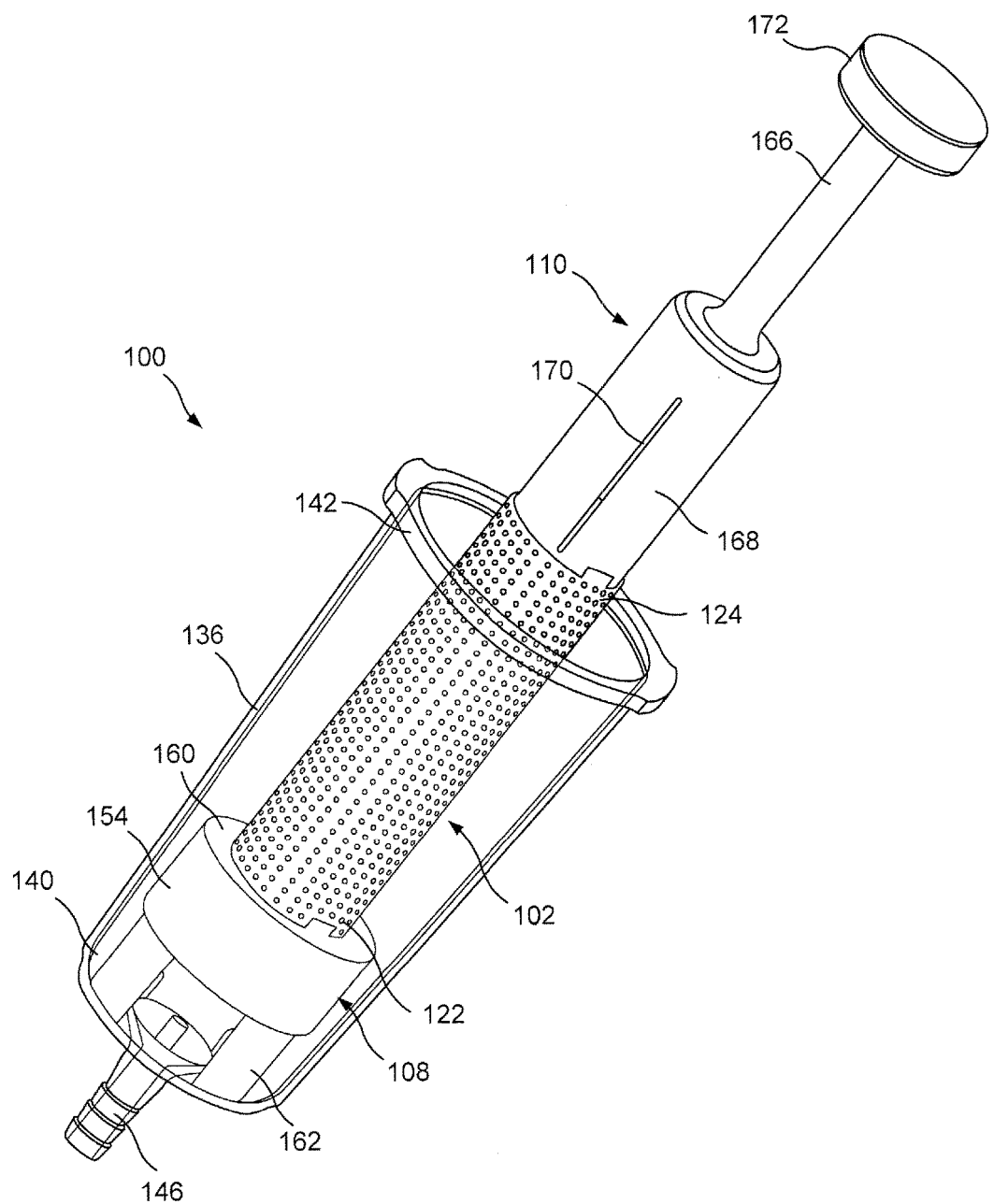
FIG. 5 shows a perspective view of the system of FIG. 1, with a plunger for packing in a bone graft.

As shown in FIGS. 3-5, the graft system 100 may further comprise a graft collection system 101 for collecting graft material and loading it into the space 132 of the container 102. The graft collection system 100 includes a canister 104 into which the container 102 is placed for filling with bone graft material. A flow directing element 108 is included within the canister 104 for guiding the graft material drawn into the canister 104 into the space 132 of the container 102. Specifically, a proximal end 142 of the canister 104, which is directed toward a patient, is connected to a suctioning element 106 while a suctioning device is connected to a distal end 140 thereof, which is directed away from the patient, to draw a suctioning force through the canister 104 and the container 102 received therein. The suctioning element 106 may be positioned at a gathering site within a body of the patient while the suctioning device at the distal end 140 is positioned outside of the patient body. The suctioning element 106 may be connected to any known reaming device (not shown) gathering graft material which is suctioned from the gathering site through a tube such as the suctioning element 106 connected to the proximal end 142 of the canister 104. The flow directing element 108 directs the flow of suctioned material (i.e., bone graft material) entering the canister 104 into the annular space 132 of the container 102 so that the collection of bone graft material and its packing into the container 102 is completed in a single step. The system 100 may optionally include a plunger 110 for packing the bone graft material in the container 102 although such manual packing may not be necessary.

The canister 104 includes a body 136 and a cover 138. The body 136 extends longitudinally from the distal end 140 to the proximal end 142 and includes a channel 144 extending therethrough sized and shaped to receive the container 102 therein. The distal end 140 may include a connector 146 such as, for example, a barb connector, for connecting the canister 104 to a tube which is connected to a secondary canister which is connected to a vacuum source. It will be understood by those of skill in the art, however, that the connector 146 may be any connecting mechanism capable of connecting the canister 104 to a vacuum tube for applying the suctioning force through the canister 104. The proximal end 142 is configured to releasably couple to the cover 138 such that the cover 138 may remain connected to the body 136 during a bone graft collection process but may be removed once the container 102 has been filled with a desired amount of the bone graft material.

The cover 138 may also include a connector 148 extending from a proximal surface of the cover 138 to connect to the suctioning element 106. The cover 138 may further include a protrusion extending distally from a distal surface of the cover 138 sized and shaped to surround the proximal end of the container 102 such that bone graft material suctioned via the suctioning element 106 is directed into the space 132 of the container 102. The suctioning element 106 may, for example, be a substantially tubular element extending from a distal end 150 that coupled to the connector 148 of the cover 138 to a proximal end 152, which may be connected to a reamer as those skilled in the art will understand so that material reamed by the reamer be drawn thereinto under suction applied through the canister 104.

The flow directing element 108 includes a base portion 154 and a shaft portion 156 extending proximally therefrom. The shaft portion 156 may be inserted into the lumen 120 of the inner sleeve 112 to direct bone graft material into the space 132 of the container 112. The base portion 154 may include a substantially planar proximal surface 160 and a plurality of legs 162 extending from a distal surface 164 thereof. The legs 162 prevents the distal surface 164 of the base portion 154 from blocking the suctioning force received via the connector 146 at the distal end 140 of the canister 104 when the container 102 and the flow directing element 108 are received in the canister 104. The shaft portion 156 may be inserted into the lumen 120 until the proximal surface 160 of the base portion 154 abuts the distal end of the container 102 and a proximal end 164 of the shaft portion 156 extends proximally past the proximal end 118 of the inner sleeve 112. The proximal end 164 of the shaft portion 156 may include a tapered tip (e.g., a conical tip) to direct bone graft material received via the suctioning element 106 away from the lumen 120 and into the space 132. The proximal surface 160 prevents bone graft material from being suctioned distally therepast such that bone graft material is collected in the space 132.

As shown in FIG. 5, once a desired amount of bone graft material has been collected in the space 132, the cover 138 and the suctioning element 106 may be detached from the body 136 of the canister 104, exposing the container 102. If desired, the user may then use the plunger 110 to pack the bone graft material in the container 102 to achieve a desired degree of packing of the bone graft material within the space 132. The plunger 110 may include a handle portion 166 and a body 168. The body 168 may extend longitudinally from a distal end (not shown) to a proximal end 170. The body 168 is sized and shaped to correspond to a size and shape of the space 132 such that the user may insert the body 168 in the space 132, moving the body 168 distally into the space 132 such that the bone graft material is packed therein. For example, the body 168 may be substantially tubular, including at least one longitudinally extending slit 172 for accommodating the rib 134 extending longitudinally between the inner and outer sleeves 112, 114. It will be understood by those of skill in the art, however, that the body 168 may be of a variety of shapes and sizes so long as the body 168 corresponds to a size and shape of the space 132 permitting the body 168 to be inserted therein to pack the bone graft material. The handle portion 166 extends proximally from the body 168 and may include, for example, a knob 172 to facilitate gripping of the handle portion 166 by the user. It will be understood by those of skill in the art, however, that the handle portion 166 may include any of a variety of configurations so long as the handle portion 166 may be gripped by a user to move the plunger 110 longitudinally relative to the container 102.

According to an exemplary technique utilizing the system 100, the user fills the container 102 with bone graft material utilizing the system 100, as described above. Specifically, the shaft 156 of the flow directing element 108 is inserted into the lumen 120 of the inner sleeve 112 so that flow directing element 108 and the container 102 are placed in the body 136 of the canister 104. The base portion 154 of the flow directing element 108 is positioned at the distal end 140 of the canister 104 such that the legs 162 raise the base portion 154 away from the distal end 140 to permit a suctioning force from an opening at the distal end 140 to pass through the canister 104. Once the container 102 and the flow directing element 108 have been properly positioned in the body 136, the cover 138 is attached to the proximal end 142 of the body 136. The connector 148 extending from the cover 138 is then coupled to the suctioning element 106 which is coupled to a reamer in a conventional manner. The connector 146 at the distal end 140 is then coupled to a suctioning device to draw a suctioning force through the canister 104 and the suctioning element 106.

Once the system 100 has been assembled, as described above, the reamer is used to harvest bone graft material which is immediately suctioned from the reamer into the canister 104 as described above. The tapered proximal end 157 of the shaft portion 156 of the flow directing element 108 directs the fluid and bone graft material received through the suctioning element 106 away from the inner lumen 120 and into the space 132 between the inner and outer sleeves 112, 114. The fluid is suctioned out of the container 102 via the holes 158 thereof such that only the bone graft material remains in the space 132. The suctioned fluid may be suctioned out of the canister 104 and into the secondary canister, which is attached to the suctioning device. Once a desired amount of bone graft material has been collected in the space 132, the user may employ the plunger 110 to pack the bone graft material in the container 102 by inserting the body 168 of the plunger 110 into the space 132 and moving the plunger 110 distally relative to the container 102 until the desired degree of packing has been achieved. After the bone material has been collected and packed in the container 102, the container 102 may be positioned in a bone defect to treat the defective bone.

As shown in FIG. 6, a container 202 according to a further embodiment of the invention is substantially similar to the container 102 described above except that the container 202 further includes a plurality of slits 276 extending partially circumferentially through portions the inner sleeve (not shown) and the outer sleeve 214. The slits 276 in this embodiment are formed in planes substantially perpendicular to a longitudinal axis L and increase the flexibility of the container 202 along the axis L facilitating handling and insertion of the container 202 into the target bone. In addition, this longitudinal flexibility compensates for slight size mismatches between the container 202 and the portion of bone it is to replace while permitting a desired amount of strain to be transferred to the bone graft to stimulate bone growth rather than shielding the bone graft from strain. As shown in FIG. 7, a container 202' according to a further embodiment of the invention includes, in place of the circumferential slots of the container 202, a plurality of slits 276' extending substantially parallel to the axis L along a portion of a length of the container 202'. The longitudinally extending slits 276' permit axial compression of the container 202' while the circumferential slits 276, as shown in FIG. 6, permit the container 202 to flex during handling and implantation. Those skilled in the art will understand that the flexibility of the container 202 will differ from that of the container 202'.

Figures 8, 9:
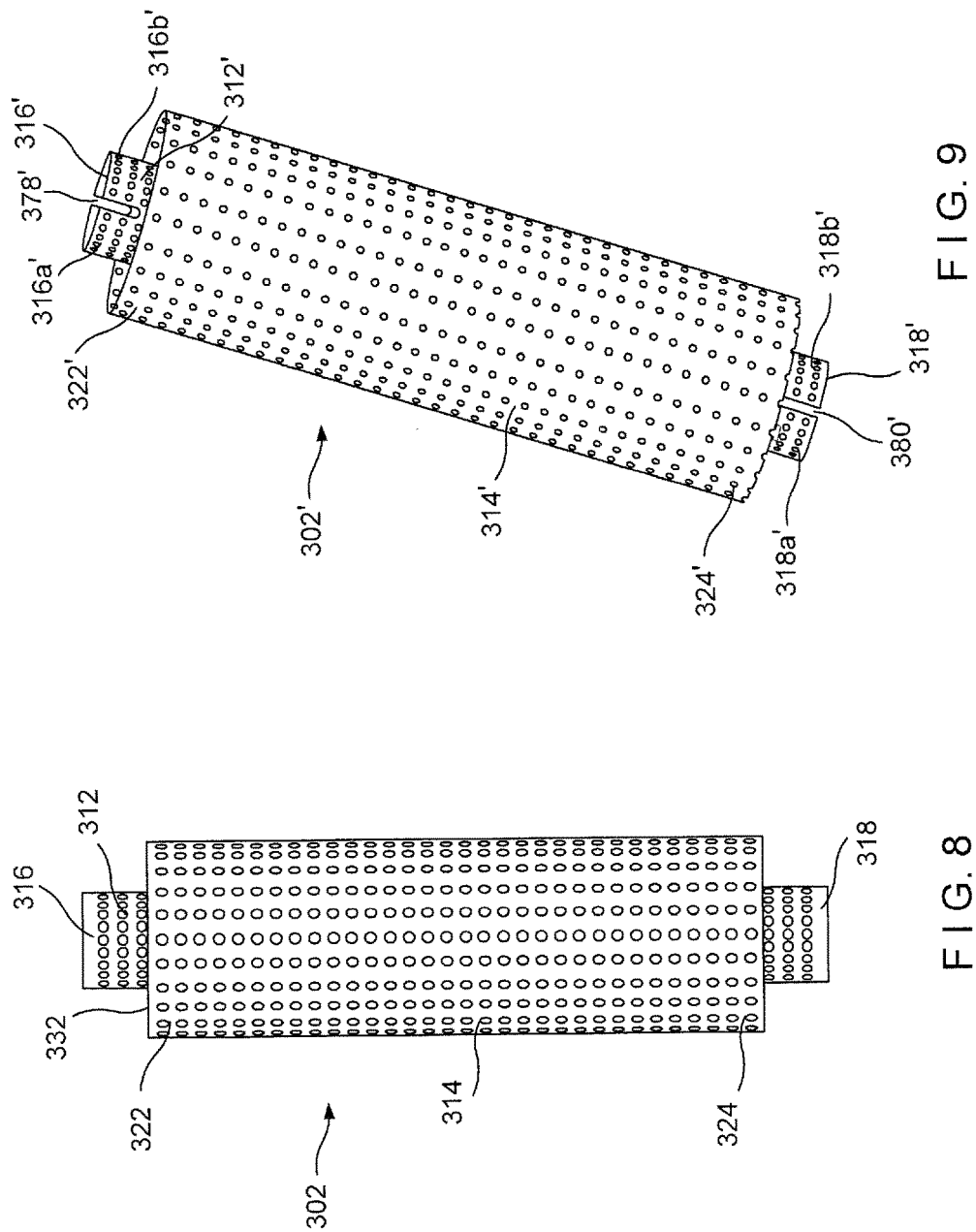
FIG. 8 shows a side view of a graft container according to a fourth exemplary embodiment of the present invention.
FIG. 9 shows a perspective view of a graft container according to a fifth exemplary embodiment of the present invention.

As shown in FIG. 8, a container 302 according to a still further embodiment of the invention is substantially similar to the container 102 described above except that the inner sleeve 312 is longer than the outer sleeve 314 such that a proximal end 316 of the inner sleeve 312 extends proximally beyond a proximal end 322 of the outer sleeve 314 and a distal end 318 of the inner sleeve 312 extends distally beyond a distal end 324 of the outer sleeve 314 so that the proximal and distal ends 316, 318 of the inner sleeve 312 may be inserted into the medullary canal of the target bone to hold the container 302 in place while permitting the bone graft material to move within a space 332 formed between the inner and outer sleeves 312, 314. Those skilled in the art will understand that a container may alternatively include an extended inner sleeve on only one end if desired.

As shown in FIG. 9, a container 302' according to a still further embodiment is substantially similar to the container 302 described above except that it includes a slot 378' extending longitudinally through a proximal end 316' of an inner sleeve 312' that extends proximally past a proximal end 322' of an outer sleeve 314'. Additionally, the container 302' includes a slot 380' extending longitudinally through a distal end 318' of the inner sleeve 312', which extends distally past a distal end 324' of the outer sleeve 314'. The slot 378' forms a pair of jaws 316a', 316b' spaced apart form one another and which may be substantially semi-circular. The jaws 316a', 316b' are biased toward the spaced apart configuration, but are movable toward one another such that the proximal end 316' for insertion into the medullary canal by pressing the 316a', 316b' slightly together. Similarly, the slot 380' splits the distal end 318' into two jaws 318a', 318b' that are spaced apart from one another and may be substantially semi-circular. The jaws 318a', 318b are biased toward a spaced condition in which they are spaced from one another but are movable relative to one another so that the jaws 318a', 318b' may be moved together and inserted into the medullary canal of the bone. Once within the medullary canal, the proximal portions 316a', 316b' and the distal portions 318a', 318b' revert to their biased, spaced apart configuration to form a friction fit with the bone locking the container 302' in place.

Figure 10:
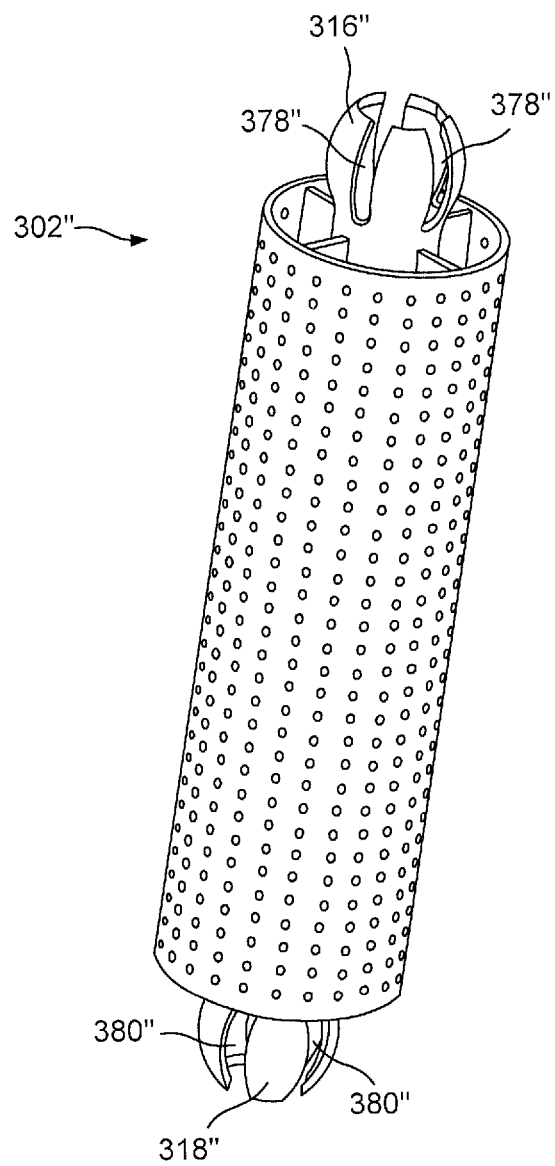
FIG. 10 shows a perspective view of a graft container according to a sixth exemplary embodiment of the present invention.

As shown in FIG. 10, a container 302'' is substantially similar to the container 302' but includes a plurality of slots 378'', 380'' extending through each of the proximal and distal ends 316'', 318'' of the inner sleeve 312''. Thus, each of the proximal and distal ends 316'', 318'' includes a plurality of jaws movable relative to one another. In addition, the proximal and distal ends 316'', 318'' are substantially spherical to facilitate insertion into the medullary canal while maintaining a friction fit with the canal once inserted.

Figure 12:
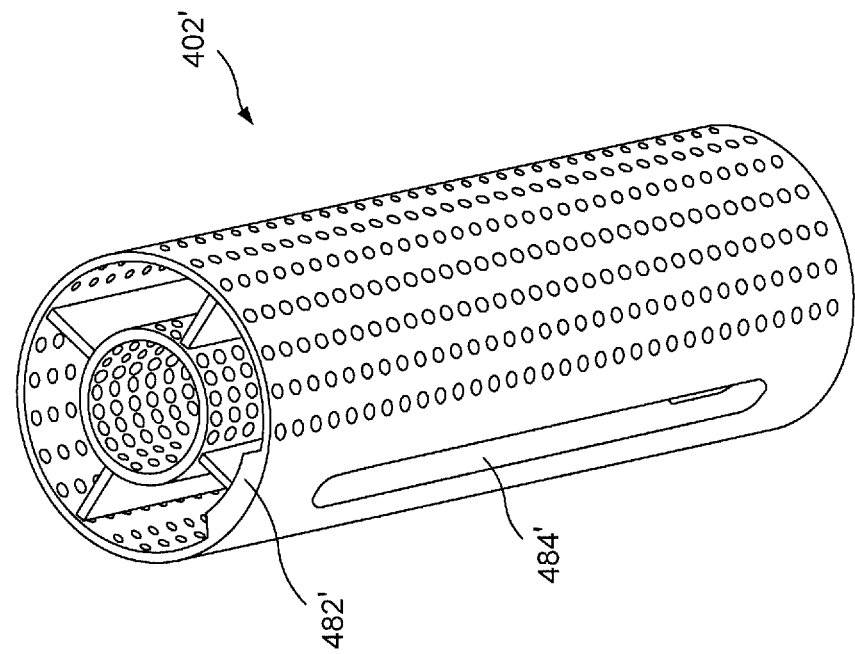
FIG. 12 shows a perspective view of a graft container according to an eighth exemplary embodiment of the present invention.
Figure 11:
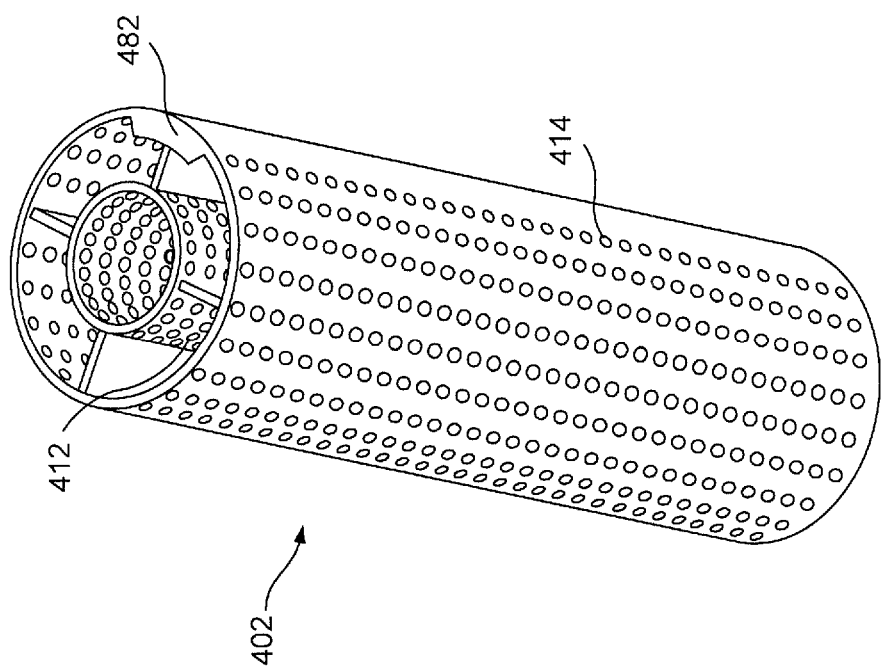
FIG. 11 shows a perspective view of a graft container according to a seventh exemplary embodiment of the present invention.

As shown in FIG. 11, a container 402 according to another exemplary embodiment of the present invention is substantially similar to the container 102 except that the outer sleeve 414 includes a reinforced section 482 extending along a length thereof. The reinforced section 482 includes a wall thicker than a wall of a remaining portion of the outer sleeve 414. The reinforced section 482 may be formed of a solid material, providing additional support such that fixation elements (e.g., screws) may be drilled therethrough when fixing a plate or other stabilizing element therealong to maintain the container 402 in position within a target portion of bone. As shown in FIG. 12, according to a further embodiment, a container 402' may also include an elongated opening 484' through a reinforced section 482' to permit insertion of fixation elements therethrough without requiring a user to drill through the thick rib section 482'.

Figure 15:
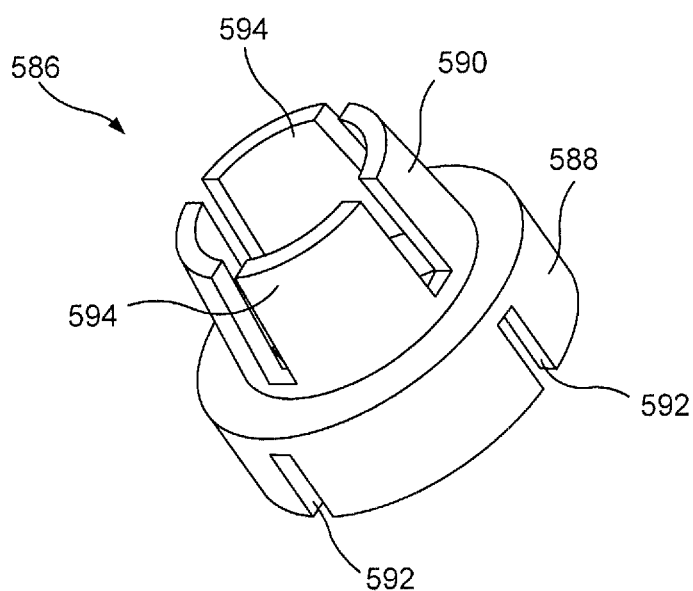
FIG. 15 shows a perspective view of the tip of FIG. 13.

According to another exemplary embodiment of the present invention, as shown in FIGS. 13-15, a system 500 is substantially similar to the system 100 except that the system 500 includes a tip 586 attachable to a proximal and/or distal end 516, 518 of an inner sleeve 512 of the container 502 for insertion into a medullary canal. Similarly to the container 102, the container 502, as shown in FIGS. 13-14, includes an outer sleeve 514 surrounding the inner sleeve 512 such that a bone graft material holding space 532 is formed therebetween. In contrast to the holes 158 shown extending through the outer wall 114, holes 558 of the container 502 may be formed as slotted perforation extending through the outer sleeve 514 and/or the inner sleeve 512. Each of the slotted perforations 558 extends about a portion of a circumference of one of the sleeves 512, 514, providing an opening for fluid flow into and/or out of the space 532. For example, the slotted perforations 558 may be approximately 1 mm wide (in a direction parallel to a longitudinal axis of the container 502) while extending circumferentially from 3 mm to 30 mm to permit nutrients, blood and irrigant flow while preventing bone graft material from passing therethrough.

As shown in FIG. 15, the tip 586 includes a first portion 588 configured to connect to one of the proximal and distal ends 516, 518 of the inner sleeve 512 and a second portion 590 adapted and configured for insertion into the medullary canal. The first portion 588 is sized and shaped to fit around the selected one of the proximal end 516 and the distal end 518 of the inner sleeve 512 and, if necessary, includes a plurality of recesses 592 sized and located to receive the ribs 534 which connect the inner and outer sleeves 512, 514. Once a desired amount of bone graft material has been packed in the space 532, the tip 586 is attached to the container 502 by sliding the first portion 588 over the selected one of the proximal and distal ends 516, 518 with the ribs 534 received in the recesses 592. The second portion 590 may include a plurality of jaws 594 spaced apart from one another such that the second portion 590 may be inserted into the canal of the bone via a friction fit as described above.

Figure 16:
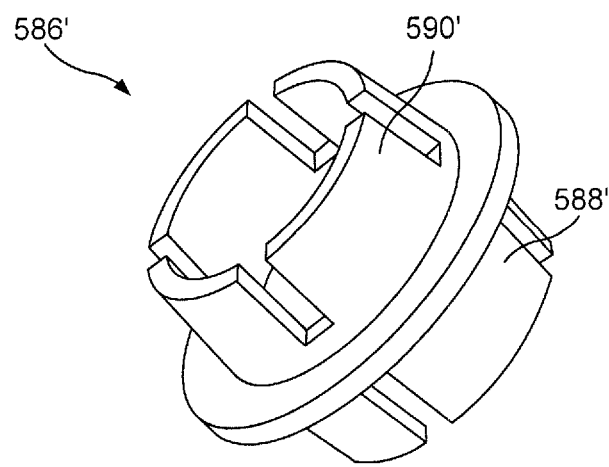
FIG. 16 shows a perspective view of a tip according to an alternate embodiment of the present invention.

In an alternate embodiment, as shown in FIG. 16, a tip 586' includes a first portion 588' for connecting the tip 586' to the container 502 and a second portion 590' for insertion into the medullary canal. The first portion 588', however, is sized and shaped to fit within a lumen 520 of the proximal and distal ends 516, 518, rather than around the sleeve 512.

Figure 17:
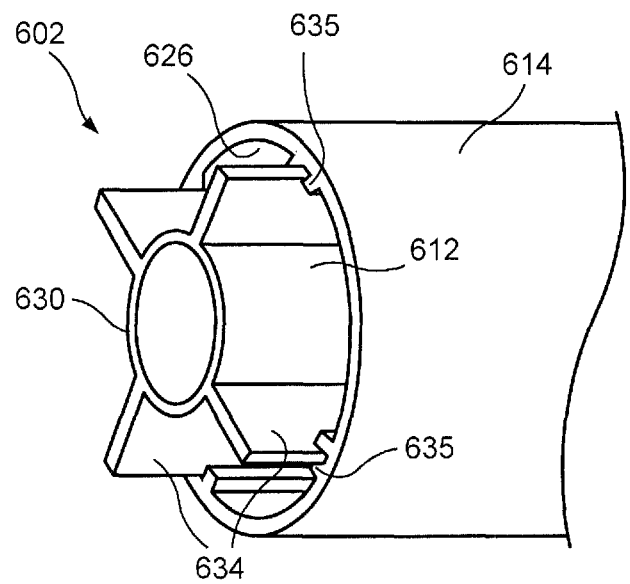
FIG. 17 shows a perspective view of a graft container according to a tenth exemplary embodiment the present invention.
Figure 18:
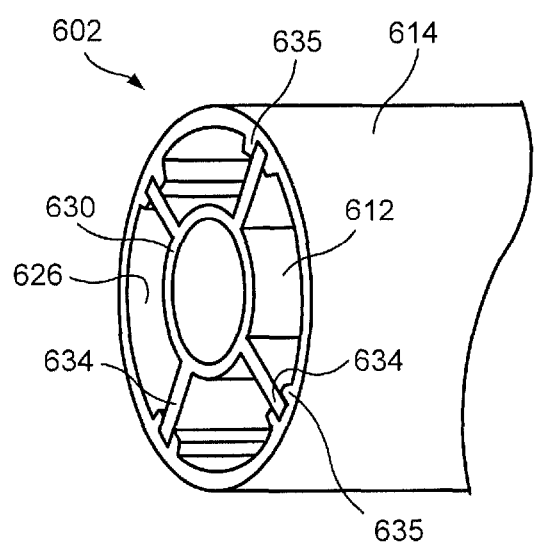
FIG. 18 shows a perspective view of the graft container of FIG. 17.

As shown in FIGS. 17-18, in another embodiment, a container 602 is substantially similar to the container 102 described above except that the container 602 includes an inner sleeve 612 and an outer sleeve 614 that are two separate parts assembled together to form the container 602. The inner sleeve 612 includes ribs 634 extending radially outward from an outer surface 630 thereof along a length of the inner sleeve 612 while the outer sleeve 614 includes corresponding rib receiving recesses 635 extending longitudinally along an inner surface 626 thereof positioned to correspond to the ribs 634. To assemble the container 602, the inner sleeve 612 is inserted into the outer sleeve 614, as shown in FIG. 17, and moved longitudinally relative thereto such that the ribs 634 are slid into the rib receiving recesses 635 of the outer sleeve 614. Once the container 602 has been assembled, as shown in FIG. 18, the container 602 may be used to collect bone graft material in the same manner described above in regard to the system 100. It will be understood by those of skill in the art that in an alternative embodiment two-part assembly embodiment, the ribs 634 may extend radially inward from the inner surface 626 of the outer sleeve 614 to be slidably received within rib receiving recesses 635 formed along the outer surface 630 of the inner sleeve 612.

Figure 19:
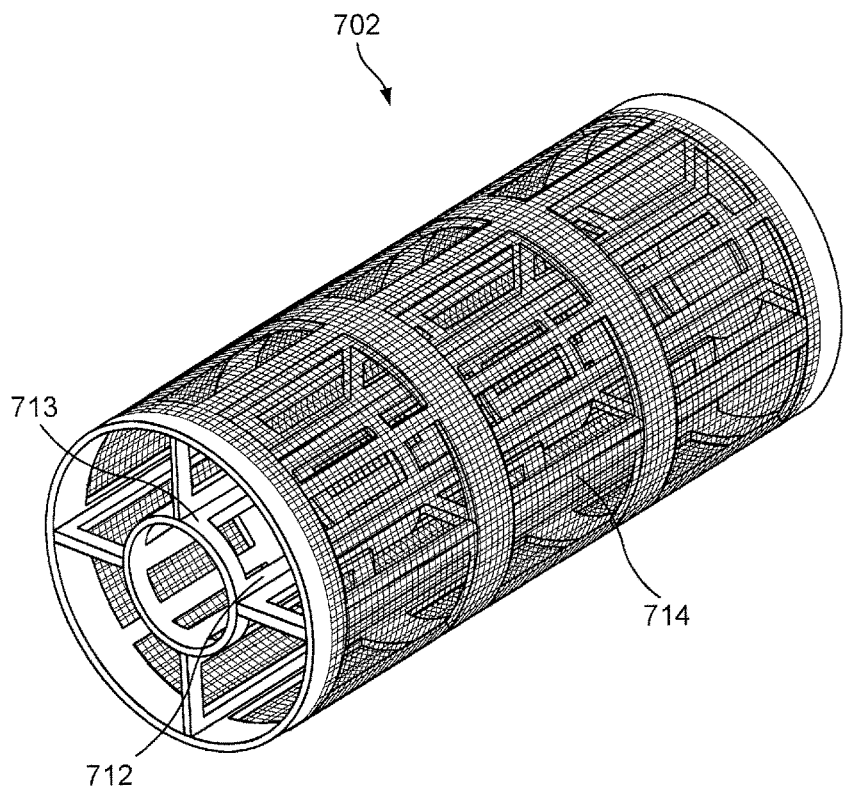
FIG. 19 shows a perspective view of a graft container according an eleventh exemplary embodiment of the present invention.

As shown in FIG. 19, a container 702 according to a further embodiment of the invention is substantially similar to the container 102 described above except that inner and outer sleeves 712, 714 thereof are formed of a mesh material fitted over a frame structure 713 to provide stability to the container 702. The mesh material permits fluid and/or nutrients to flow through the container 702 while preventing the bone graft material from falling therethrough. The mesh material may be formed of, for example, a woven band or a strip of PCL bonded to the frame structure 713 of the container 702.

It will be understood by those of skill in the art that any of the embodiments of the containers 102-702 described above may be sized and shaped for the treatment of various bones. For example, as shown in a cross-sectional depiction of a container 802 in FIG. 20, the container 802 is particularly suited for tibial applications, comprising an inner sleeve 812 substantially circular in cross-section and an outer sleeve 814 that is substantially triangular in cross-section. In a preferred embodiment, the inner and outer sleeves 812, 814 may be connected by three ribs 834 extending longitudinally therebetween, with each rib 832 extending from a corner of the substantially triangular outer sleeve 814 to an outer surface of the inner sleeve 812 to form three sections of space 832 between the inner and outer sleeves 812, 814. It will be understood by those of skill in the art that the container 802 may include any number of ribs 834. For example, the container 802 may include two ribs 834 such that two sections of space 832 are created between the inner and outer sleeves 812, 814.

Figures 20, 21:
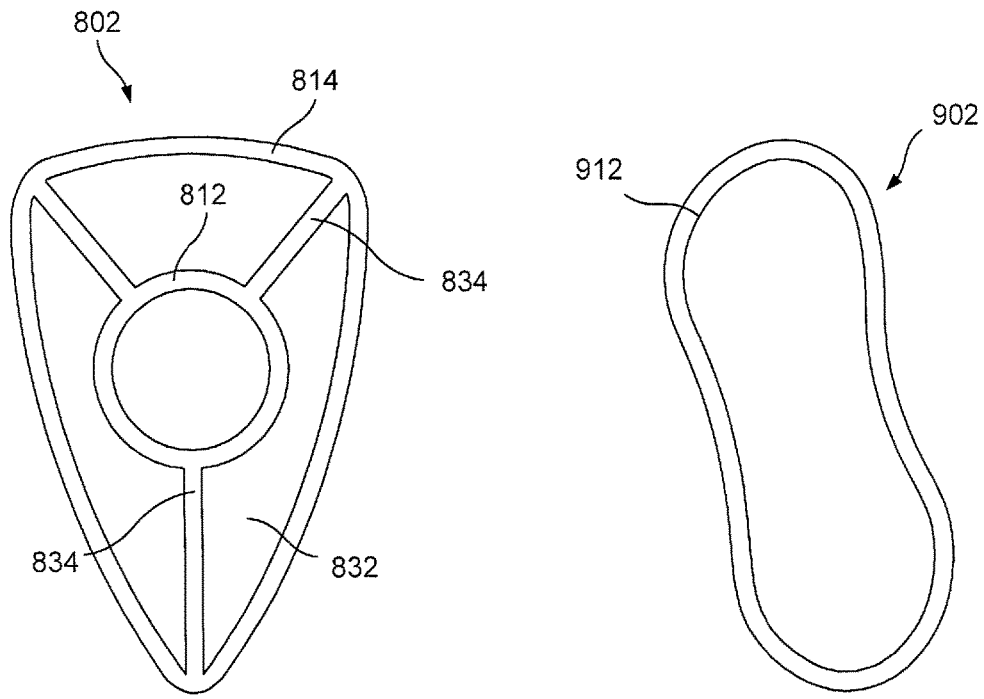
FIG. 20 shows a cross-sectional view of a graft container according to a twelfth exemplary embodiment of the present invention.
FIG. 21 shows a cross-sectional view of a graft container according to a thirteenth exemplary embodiment of the present invention.
Figure 22:
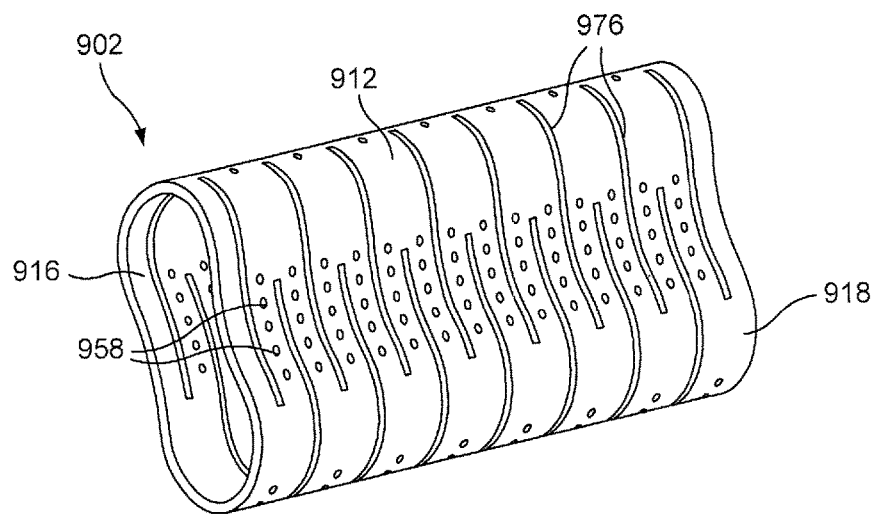
FIG. 22 shows a perspective view of the graft container of FIG. 21.

In another embodiment, a container 902, as shown in FIGS. 21-22, is sized and shape for mandibular applications. The container 902 may have an irregular cross-section, as shown in FIG. 21, and may comprise a single sleeve 912 extending longitudinally from a proximal end 916 to a distal end 918. Although the container 902 is shown as including a single sleeve, it will be understood by those of skill in the art that the container 902 may include any of the features described above in regard to the inner and outer sleeves of the above-described embodiments, including a second sleeve. For example, the container 902 may include holes 958 for permitting nutrients and/or fluid to pass therethrough and slits 976 extending therethrough around a portion of a perimeter thereof for flexibility.

Figure 23:
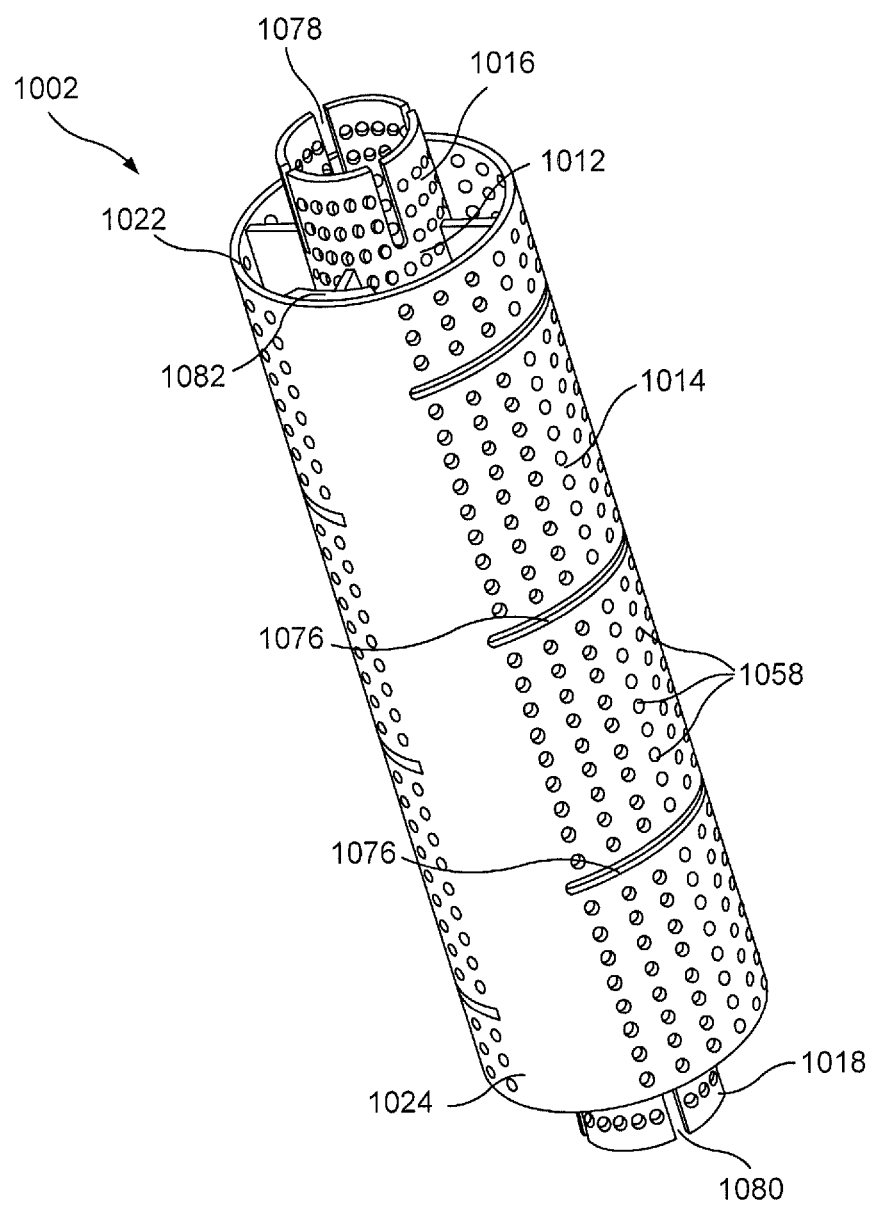
FIG. 23 shows a perspective view of a graft container according to a fourteenth exemplary embodiment of the present invention.

It will be understood by those of skill in the art that any of the features described above in regard to the various embodiments of the container 102-902 may be combined in a single container, if so desired. For example, as shown in FIG. 23, a container 1002 may include an inner sleeve 1012 longer than an outer sleeve 1014 such that a proximal end 1016 of the inner sleeve 1012 extends proximally past a proximal end 1018 of the outer sleeve 1014 and a distal end 1018 of the inner sleeve 1012 extends distally past a distal end 1024 of the outer sleeve 1014. The proximal and distal ends 1016, 1018 are configured to be inserted into a canal of a defective bone and may further include one or more longitudinal slits 1078, 1080 extending through a portion thereof, respectively, to provide a friction fit within the canal of the bone. The container 1002 may also include holes 1058 for permitting flow therethrough and horizontal slits 1076 providing flexibility extending through at least one of the inner and outer sleeve 1012, 1014. In addition, the container may also include a reinforced section 1082 extending along a length of the outer sleeve 1014 for permitting fixation elements to be drilled and/or inserted therethrough. It will be understood by those of skill in the art that other combinations of features, shapes, sizes, etc. described with respect to the exemplary embodiments of the present invention, which are not specifically described herein, are also possible.

As shown in FIGS. 24-25, according to another embodiment of the present invention, a graft container 1102 substantially similar to the graft container 102 described above, is divided along a length thereof to form two clam-shell portions 1102a, 1102b connected to one another via a hinge 1174. The first and second clam-shell portions 1102a, 1102b may pivot with respect to one another about the hinge 1174 such that container 1102 is movable between an open configuration in which the first and second clam-shell portions 1102a, 1102b are pivoted away from one another and a closed configuration, in which the clam-shell portions 1102a, 1102b are pivoted into engagement with one another. Thus, the container 1102 may be applied to a target portion of a bone after insertion of an intramedullary rod. In particular, in the open configuration, the container 1102 may be positioned around a portion of the intramedullary rod. Once the container 1102 has been properly positioned, the container 1102 may be moved to the closed configuration such that the intramedullary rod is encased between the first and second clam-shell portions 1102a, 1102b.

Similarly to the container 102, each of the first and second portions 1102a, 1102b includes an inner sleeve portion 1112a, 1112b and an outer sleeve portion 1114a, 1114b forming a space 1132a, 1132b therebetween for holding bone graft material therein. A channel 1176 formed between the inner sleeve portions 1112a, 1112b, when the inner sleeve portions 1112a, 1112b are joined together in the closed configuration, is sized and shaped to accommodate the intramedullary rod therein. Thus, when the container 1102 is being positioned around the intramedullary rod, the container 1102 is positioned such that the rod is seated in one portion of the channel 1176. The container 1102 may then be moved to the closed configuration such that the rod is encased in the opening 1176 between the first and second clam-shell portions 1102a, 1102b. The inner sleeve portions 1112a, 1112b and outer sleeve portions 1114a, 1114b may also include a plurality of openings 1158 extending therethrough to permit nutrients to flow into and out of the container 1112. The plurality of openings 1158 may be formed as substantially circular holes, as shown in the embodiment of FIG. 1, and/or slotted perforations, as shown in the embodiment of FIG. 13.

The hinge 1174 may be arranged on the container 1102 to join opposing edges of the outer sleeve portions 1114a, 1114b of the first and second clam-shell portions 1102a, 1102b together. The hinge 1174 may be, for example, a bonded flexible or woven resorbable PLA strip applied to the opposing edges. Alternatively, the binge 1174 may be a suture joining the opposing edges together. It will be understood by those of skill in the art, however, that the hinge 1174 may be any of a variety of elements joining opposing edges of the outer sleeves portions 1114a, 1114b of the clam-shell portions 1102a, 1102b together. Similarly, once the container 1102 has been applied over a portion of the intramedullary rod in a target portion of bone and moved to the closed configuration, the clam-shell portions 1102a, 1102b may be similarly maintained in the closed configuration by applying a woven strip or suturing opposing edges of the open side of the clam-shell portions 1102a, 1102b together. The hinge 1174 may also be formed of a resorbable material. It will be understood by those of skill in the art, however, that the container 1102 may be maintained in the closed configuration using any known locking mechanism or joining element known in the art. It will also be understood by those of skill in the art, the first and second clam-shell portions 1102a, 1102b may not pivot about the hinge 1174. Rather, the first and second clam-shell portions 1102a, 1102b may be positioned along the desired portion of bone and joined together in a desired configuration via a suture and or a woven strip.

The container 1102 may be similarly used with the graft collection system 101, described above in regard to the graft system 100, to collect graft material in the spaces 1132a, 1132b. Since the container 1102 is substantially similar to the container 102 in the closed configuration, the container 1102 is simply moved to the closed configuration and placed in the canister 104, as described above.

Where the container 1102 is being used to treat a bone such as, for example, a femur, each of the first and second portions 1102a, 1102b may be substantially semi-cylindrical and attached on one side via the hinge 1174 so that when the container 1102 is in the closed configuration, the container 1102 is substantially cylindrical. It will be understood by those of skill in the art, however, that the container 1102 may be any of a variety of shapes and sizes selected to fit a target bone. For example, as shown in FIG. 26, a container 1102' may be a substantially triangular shape suited for tibial applications. The container 1102', may be substantially similar to the container 802 described above and shown in FIG. 20, but divided along a length thereof to form two clam-shell portions 1102a', 1102b'.

Figure 28:
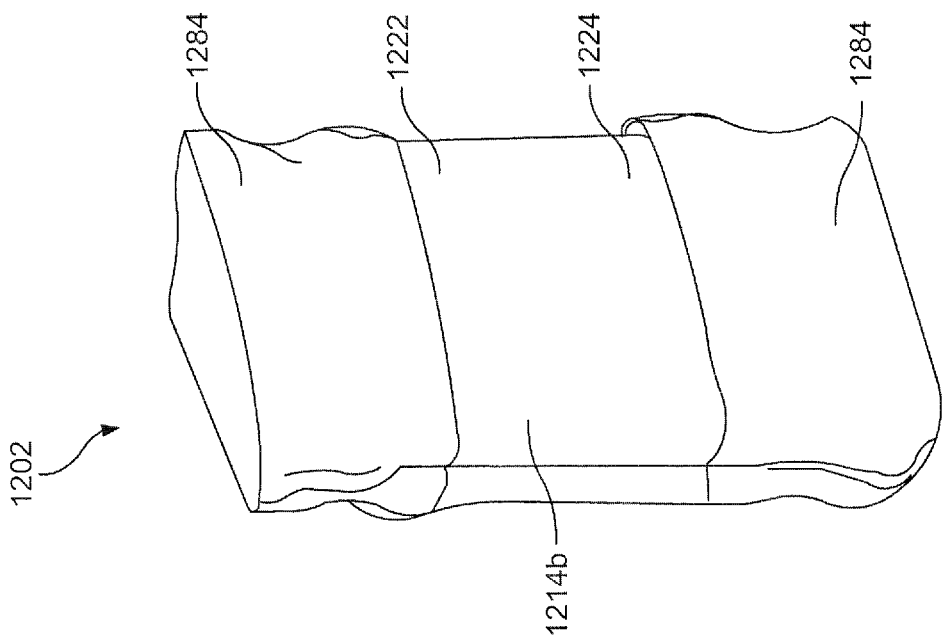
FIG. 28 shows a perspective view of a graft container according to a further embodiment of the present invention.
Figure 27:
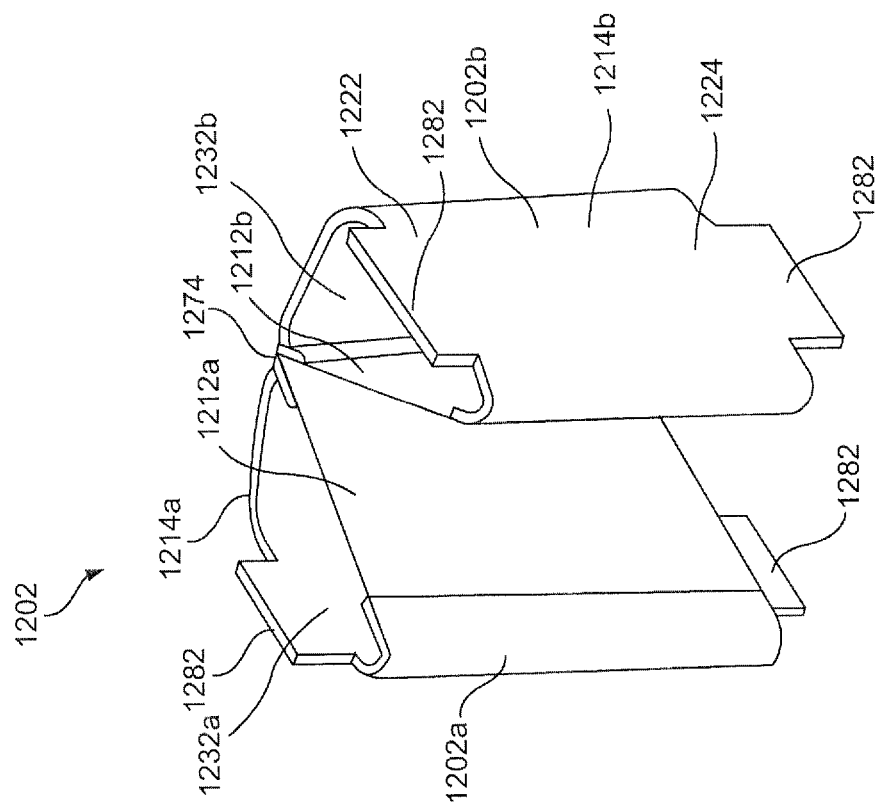
FIG. 27 shows a perspective view of a graft container according to a seventeenth exemplary embodiment of the present invention.

As shown in FIGS. 27 and 28, a container 1202 is substantially similar to the container 1102, described above, comprising two clam-shell portions 1202a, 1202b which pivot with respect to one another about a hinge 1274 between an open configuration and a closed configuration. Similarly to the container 1102, the first and second clam-shell portions 1202a, 1202b include inner sleeve portion 1212a, 1212b and outer sleeve portions 1214a, 1214b forming a space 1232a, 1232b therebetween for holding bone graft material therein. The container 1202 may be positioned over a target portion of bone in the open configuration with the first and second clam-shell portions 1202a, 1202b pivoted away from one another, and moved to the closed configuration with the first and second clam-shell portions 1202a, 1202b pivoted toward one another to enclose an intramedullary nail between the inner sleeve portions 1212a, 1212b. Inner sleeve portions 1212a, 1212b of the first and second clam-shell portions 1202a, 1202b, respectively, are formed of a flexible material such as, for example, polycaprolactone (PCL), such that the inner sleeve portions 1212a, 1212b wrap about the intramedullary nail as it is applied to a target portion of a bone without interference that might result from the application of a rigid structure over the nail. That is, the flexible nature of the inner sleeve portions 1212a and 1212b allow the container 1202 to be placed over a bone even where the nail is not centered within the bone—i.e., the flexibility of the inner sleeve portions 1212a and 1212b allows the container 1202 to adapt to a situation where a variation in the positioning of the medullary canal in a portion of bone to be treated has moved the nail. Thus, such a container 1202 may be used in more situations than a rigid container. The outer sleeve portions 1214a, 1214b are preferably rigid, but may also be formed of a flexible material. Although not shown, the inner and/or outer sleeve portions 1212a, 1212b, 1214a, 1214b may also include pores extending therethrough to permit evacuation of blood and irrigation fluids during graft material collection, while also permitting nutrients to flow into the bone graft material collected in the space 1232a, 1232b from radially outside and inside the container 1202.

As shown in FIG. 27, the container 1202 may also include a tab 1282 extending longitudinally from each of proximal and/or distal ends 1222, 1224, respectively, of the outer sleeve portions 1214a, 1214b. Tabs 1282 may be attached to ends of the target bone, between which the container 1202 is being positioned. The tabs 1282 may be attached to the bone via, for example, resorbable tacks, to enhance stabilization on bone ends. In a further embodiment, as shown in FIG. 28, the container 1202 may also include proximal and/or distal flexible cuffs 1284 attached to the proximal and/or distal ends 1222, 1224 of the outer sleeve portions 1214a, 1214b for additional stabilization. The flexible cuffs 1284 may be formed of any flexible material such as, for example, PCL, and are configured to extend about bone ends between which the container 1202 is positioned. The cuffs 1284 may be particularly useful for fixing the container 1202 between bone ends that are uneven. The cuffs 1284 may be closed about the bone ends using for example, a suture closing.

Although the outer sleeve portions 1214a, 1214b are shown to have a substantially triangular cross-sectional shape in the closed configuration, it will be understood by those of skill in the art that the outer sleeve portions 1214a, 1214b may take any of a variety of shapes and sizes depending on a type of bone in which the container 1202 is desired to be placed within. In addition, although the exemplary embodiment described above specifically describes a flexible inner sleeve in regard to a container including two clam-shell portions, it will be understood by those of skill in the art that a flexible inner sleeve and/or a flexible outer sleeve may be incorporated into any of the container embodiments 102-1102 described above.

It will be understood by those of skill in the art that all of the containers described above may be utilized with the graft collection system 101, described above with regard to the system 100. To accommodate those containers that are not cylindrical such as, for example, containers 802, 902, 1102' and 1202, described above, the graft collection system 101 may further comprise an adaptor 186, as shown in FIG. 29, extending from a proximal end 188 to a distal end 190 and including a lumen therethrough. The distal end 190 is sized and shaped to be coupled to a proximal end of the container (e.g., triangular) such as the container 1202, while the proximal end 188 is sized and shaped (e.g., circular) to be coupled to a portion of the cover 138 such that bone graft material suctioned via the suctioning element 106 is directed into the graft collection space between the non-cylindrical outer sleeve and the inner sleeve of the container. It will be understood by those of skill in the art that the adaptor 186 may be available in a variety of sizes and shapes to accommodate containers suited for any of a variety of types of bone, such as for the tibial and the mandibular applications.

Figure 30:
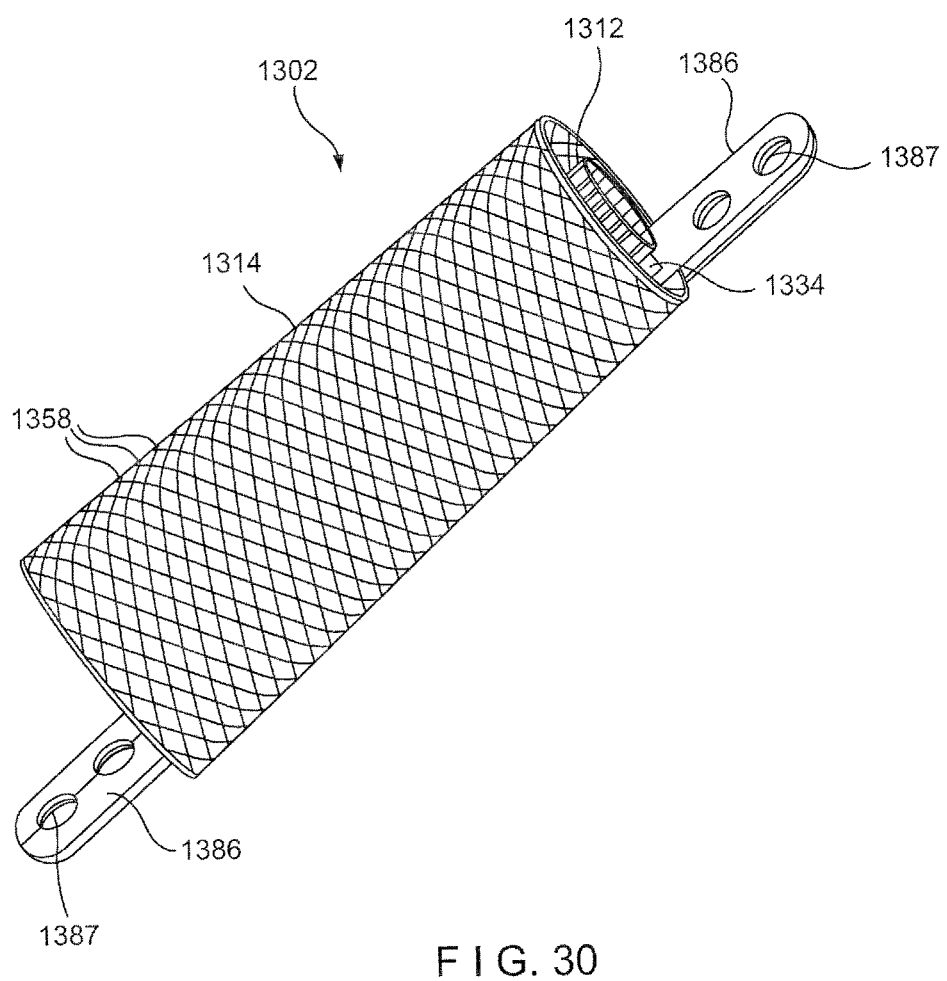
FIG. 30 shows a perspective view of a graft container formed using an exemplary method of the present invention.

According to another exemplary method of the present invention, a custom bone graft container 1302, as shown in FIG. 30, may be formed by laser sintering metal or any other suitable material to conform to a patient's anatomy based on, for example, a CT scan of a target portion of bone. In an exemplary embodiment, a surgeon may test a plastic model of the graft container 1302 before forming the graft container 1302 out of the desired metal material. Thus, a plastic model of inner and outer sleeves 1312, 1314 may be formed. The plastic model of the inner sleeve 1312 is sized and shaped to correspond to a medullary canal (e.g., a size and shape of an intramedullary nail extending therethrough) while the plastic model of the outer sleeve 1314 is sized and shaped to correspond to an exterior surface of the bone. The plastic models may then be tested on the patient so that any required changes to the size and shape of either of the inner and outer sleeves 1312, 1314 of the graft container 1302 may be identified. A final plastic prototype of the inner and outer sleeves 1312, 1314 may be formed, incorporating any requires changes.

The inner sleeve 1312 may be formed to a shape of the medullary canal of the bone and to accommodate an intramedullary nail extending therethrough. Where a plastic model has been utilized, the inner sleeve 1312 may be sintered to correspond to the final prototype of the inner sleeve. The inner sleeve 1312 may be formed to also include a longitudinal slot (not shown) extending therealong such that the inner sleeve 1312 may be opened and positioned about the intramedullary nail. An outer sleeve 1314 may be similarly laser sintered from a laser material to conform to the shape of the patient's bone and/or the final plastic prototype of the plastic model. The outer sleeve 1314 may include proximal and/or distal tabs 1386 extending therefrom and including at least one borehole 1387 extending therethrough to facilitate attachment to an exterior of ends of the bone between which the outer sleeve 1314 is positioned. Similarly to the containers described above, the inner and/or outer sleeves 1312, 1314 may be formed with a plurality of holes 1358 extending therethrough. In another exemplary embodiment, the graft container 1302 may, for example, be fabricated in similarly appropriate medical grade materials using additive manufacturing processes.

The inner and outer sleeves 1312, 1314 may be connected to one another via an attachment tab 1334 extending therebetween such that the inner sleeve 1312 is positioned around a portion of the intramedullary nail between ends of the target area of the bone and the outer sleeve 1314 is similarly positioned between the ends of the bone. A bone graft material may be packed in a space between the inner and outer sleeves 1312, 1314 by, for example, packing the material through proximal and/or distal ends thereof or through the holes 1358 extending through the outer sleeve 1314. The outer sleeve 1314 may be similarly attached to the bone by inserting fixation elements through the boreholes 1387 extending through the tabs 1386. In a further embodiment, a cuff may also be attached to the proximal and/or distal ends 1322, 1324 of the outer sleeve 1314. The cuff may be substantially similar to the cuff 1284 described above in regard to the container 1202 and may be positioned to extend about ends of the target bone. A suture may be used to fix the cuff about the bone ends.

In an alternate embodiment, the graft container 1302 may only be comprised of the outer sleeve 1314, which is sintered to correspond in size and shape to the target bone of the CT scan. In this embodiment, bone graft material may be packed within the outer sleeve 1314 about the intramedullary nail. As described above, the outer sleeve 1314 may be affixed to the bone via the boreholes 1387 in the tabs 1386.

It will be understood by those of skill in the art that various modifications and variations can be made in the structure and methodology of the present invention, without departing from the spirit or scope of the invention. Thus, it is intended that the present invention cover the modifications and variations of this invention provided that they come within the scope of the appended claims and their equivalents.

The present invention relates to a method for forming a custom-fit bone graft container, comprising obtaining a CT image of a bone of a patient; forming a first model of a bone graft container corresponding in size and shape to a target portion of the bone based on the CT image; comparing the first model of the bone graft container to the target portion of the bone to identifying any required changes thereto to conform the first model to the size and shape of the target portion of the bone; incorporating any required changes into the first model to form a first prototype; and laser melting or sintering a metal material to form a custom bone graft container corresponding in size and shape to the first prototype.

What is claimed is:

1. A device for containing bone graft material, comprising:
    an inner sleeve extending longitudinally from a proximal end to a distal end; and
    an outer sleeve surrounding the inner sleeve and extending longitudinally from a proximal end to a distal end such that a bone graft collecting space is formed therebetween, the proximal end of the of the inner sleeve extending proximally past the proximal end of the outer sleeve and the distal end of the inner sleeve extending distally past the distal end of the outer sleeve, the proximal and distal ends of the inner sleeve being sized and shaped for insertion into a medullary canal of a bone within which the device is to be employed.

2. The device of claim 1, wherein at least one of the inner and outer sleeves includes a plurality of openings extending therethrough sized to permit fluids to pass therethrough while preventing the passage of bone graft material therethrough.

3. The device of claim 1, wherein one of the inner and outer sleeves includes a plurality of slits extending through a portion of a circumference thereof to permit the device to flex along a longitudinal axis thereof.

4. The device of claim 1, wherein a contour of the inner sleeve is selected to substantially match a contour of a medullary canal of a bone within which the device is to be employed.

5. The device of claim 1, wherein a contour of the outer sleeve is selected to substantially match a contour of an exterior surface of a bone within which the device is to be employed.

6. The device of claim 1, wherein one of the proximal and distal ends of the inner sleeve includes a longitudinal slit extending therethrough to separate the one of the proximal and distal ends into opposed jaws biased toward a spaced configuration in which the jaws extend across a space larger than a medullary canal within which they are to be received, the jaws being flexibly movable toward one another to an insertion configuration in which the one of the proximal and distal ends is sized for insertion into a medullary canal so that, upon release within a medullary canal the jaws create a friction fit therewith.

7. The device of claim 1, wherein a proximal tip of the proximal end is rounded to facilitate insertion into a medullary canal.

8. The device of claim 1, wherein the outer sleeve includes a reinforced section extending longitudinally along a portion of a length thereof, the reinforced section having a wall thickness greater than that of a remaining portion of the outer sleeve.

9. The device of claim 8, wherein the outer sleeve includes a slot extending through the reinforced section sized to receive a fixation element therethrough.

10. The device of claim 1, wherein the inner and outer sleeves are integrally formed and connected to one another via a plurality of ribs extending longitudinally therebetween.

11. The device of claim 1, wherein the inner and outer sleeves are removably connected to one another.

12. The device of claim 1, wherein a lumen of the inner sleeve is sized and shaped to accommodate an intramedullary rod therein.

\* \* \* \* \*

UNITED STATES PATENT AND TRADEMARK OFFICE
CERTIFICATE OF CORRECTION

PATENT NO. : 9,782,259 B2  
APPLICATION NO. : 14/463404  
DATED : October 10, 2017  
INVENTOR(S) : Mikhail et al.

It is certified that error appears in the above-identified patent and that said Letters Patent is hereby corrected as shown below:

In the Claims

Claim 1, Column 14, Line 30:
"therebetween, the proximal end of the of the inner" should read "therebetween, the proximal end of the inner".

Signed and Sealed this
First Day of May, 2018

Andrei Iancu
*Director of the United States Patent and Trademark Office*